US00RE49114E

(19) United States
(12) Reissued Patent
Newton

(10) Patent Number: US RE49,114 E
(45) **Date of Reissued Patent: *Jun. 28, 2022**

(54) ELECTRONIC CIGARETTE WITH LIQUID RESERVOIR

(71) Applicant: JUUL Labs, Inc., San Francisco, CA (US)

(72) Inventor: Kyle D. Newton, Southlake, TX (US)

(73) Assignee: JUUL Labs, Inc., San Francisco, CA (US)

( * ) Notice: This patent is subject to a terminal disclaimer.

(21) Appl. No.: 16/359,938

(22) Filed: Mar. 20, 2019

Related U.S. Patent Documents

Reissue of:
(64) Patent No.: 9,596,887
Issued: Mar. 21, 2017
Appl. No.: 14/219,426
Filed: Mar. 19, 2014

U.S. Applications:
(63) Continuation of application No. 13/955,153, filed on Jul. 31, 2013, now Pat. No. 8,707,965, which is a continuation of application No. 13/157,024, filed on Jun. 28, 2011, now Pat. No. 8,528,569.

(51) Int. Cl.

| | |
|---|---|
| ***A24F 40/44*** | (2020.01) |
| ***A24F 40/485*** | (2020.01) |
| ***A24F 40/42*** | (2020.01) |
| ***A61M 15/06*** | (2006.01) |
| ***A24F 40/10*** | (2020.01) |

(52) U.S. Cl.
CPC ..... *A24F 40/44* (2020.01); *A24F 40/42* (2020.01); *A24F 40/485* (2020.01); *A61M 15/06* (2013.01); *A24F 40/10* (2020.01)

(58) Field of Classification Search
CPC .. A61M 15/06; B01D 19/0047; B05B 7/1693; A24B 15/167; A24C 5/12; A24F 47/00; A24F 47/002
See application file for complete search history.

(56) References Cited

U.S. PATENT DOCUMENTS

| | | | |
|---|---|---|---|
| 3,085,145 | A | 4/1963 | Wray, Jr. |
| 3,918,451 | A | 11/1975 | Steil |
| 3,934,117 | A | 1/1976 | Schladitz |

(Continued)

FOREIGN PATENT DOCUMENTS

| | | | |
|---|---|---|---|
| AU | 2014208287 | B2 | 12/2016 |
| AU | 2017202891 | B2 | 5/2019 |

(Continued)

*Primary Examiner* — Norca L. Torres Velazquez
(74) *Attorney, Agent, or Firm* — Mintz Levin Cohn Ferris Glovsky and Popeo, P.C.

(57) ABSTRACT

An electronic cigarette including an housing that has a mouthpiece with an aerosol outlet, and an atomizer disposed within an atomizing chamber. The atomizer selectively generates an aerosol of the liquid in response to suction pressure at the aerosol outlet. The atomizing chamber has an air inlet, an atomizer outlet coupled to the aerosol outlet, and a first wick aperture. A liquid reservoir is disposed within the housing, which is sealably separated from the atomizing chamber. A wick disposed through the first wick aperture between the liquid reservoir and the atomizing chamber and it is configured to transfer the liquid by capillarity from the liquid reservoir to the atomizer.

195 Claims, 7 Drawing Sheets

(56) References Cited

U.S. PATENT DOCUMENTS 4,171,000 A 10/1979 Uhle
4,745,705 A 5/1988 Yamamoto et al.
4,793,365 A 12/1988 Sensabaugh, Jr. et al.
4,811,731 A 3/1989 Newell et al.
4,941,236 A 7/1990 Sherman et al.
4,947,874 A 8/1990 Brooks et al.
4,947,875 A 8/1990 Brooks et al.
4,993,436 A 2/1991 Bloom, Jr.
5,042,509 A 8/1991 Banerjee et al.
5,117,482 A 5/1992 Hauber
5,144,962 A 9/1992 Counts et al.
5,261,424 A 11/1993 Sprinkel, Jr.
5,269,327 A 12/1993 Counts et al.
5,479,948 A 1/1996 Counts et al.
5,666,977 A 9/1997 Higgins et al.
5,682,050 A 10/1997 Williams
5,865,185 A 2/1999 Collins et al.
6,090,082 A 7/2000 King et al.
6,155,268 A * 12/2000 Takeuchi ..... A24F 47/008 131/273
6,443,146 B1 9/2002 Voges
6,516,796 B1 2/2003 Cox et al.
6,532,965 B1 3/2003 Abhulimen et al.
6,708,846 B1 3/2004 Fuchs et al.
6,772,756 B2 8/2004 Shayan
7,173,222 B2 2/2007 Cox et al.
7,318,435 B2 1/2008 Pentafragas
D590,990 S 4/2009 Hon
7,726,320 B2 6/2010 Robinson et al.
7,802,569 B2 9/2010 Yeates et al.
7,913,688 B2 3/2011 Cross et al.
8,205,622 B2 6/2012 Pan
8,251,060 B2 8/2012 White et al.
8,365,742 B2 2/2013 Hon
8,371,310 B2 2/2013 Brenneise
8,499,766 B1 8/2013 Newton
8,522,776 B2 9/2013 Wright et al.
8,528,569 B1 9/2013 Newton
8,752,545 B2 6/2014 Buchberger
8,869,792 B1 10/2014 Lee
8,893,726 B2 11/2014 Hon
8,899,240 B2 12/2014 Mass
8,978,663 B2 3/2015 Newton
8,991,402 B2 3/2015 Bowen et al.
9,072,321 B2 7/2015 Liu
9,095,175 B2 8/2015 Terry et al.
9,277,768 B2 3/2016 Xiu
9,315,890 B1 4/2016 Frick et al.
9,345,541 B2 5/2016 Greeley et al.
9,420,829 B2 8/2016 Thorens et al.
9,504,279 B2 11/2016 Chen
9,555,203 B2 1/2017 Terry et al.
9,743,691 B2 8/2017 Minskoff et al.
9,801,413 B2 10/2017 Zhu
9,814,263 B2 11/2017 Cochand et al.
9,844,234 B2 12/2017 Thorens et al.
9,974,743 B2 5/2018 Rose et al.
9,999,250 B2 6/2018 Minskoff et al.
2002/0043262 A1 4/2002 Langford et al.
2002/0078951 A1 6/2002 Nichols et al.
2002/0088469 A1 7/2002 Rennecamp
2003/0226837 A1 12/2003 Blake et al.
2004/0050382 A1 3/2004 Goodchild
2005/0016550 A1 1/2005 Katase
2005/0134215 A1 6/2005 Bozzone et al.
2005/0172976 A1 8/2005 Newman et al.
2006/0196518 A1 9/2006 Hon
2007/0045288 A1 3/2007 Nelson
2007/0074734 A1 4/2007 Braunshteyn et al.
2007/0229025 A1 10/2007 Tsai et al.
2007/0267031 A1 11/2007 Hon
2007/0277816 A1 12/2007 Morrison et al.
2007/0283972 A1 12/2007 Monsees et al.
2008/0023003 A1 1/2008 Rosenthal
2008/0029095 A1 2/2008 Esser
2008/0257367 A1 10/2008 Paterno et al.
2008/0302374 A1 12/2008 Wengert et al.
2009/0095287 A1 4/2009 Emarlou
2009/0095311 A1 4/2009 Han
2009/0133691 A1 5/2009 Yamada et al.
2009/0272379 A1 11/2009 Thorens et al.
2009/0293892 A1 12/2009 Williams et al.
2009/0302019 A1 12/2009 Selenski et al.
2010/0031967 A1 2/2010 Inagaki
2010/0031968 A1 2/2010 Sheikh et al.
2010/0194337 A1 8/2010 Opolka
2010/0200008 A1 8/2010 Taieb
2010/0207576 A1 8/2010 Elizalde Rodarte
2010/0253279 A1 10/2010 Matthias
2011/0011396 A1* 1/2011 Fang ..... A24F 47/002 128/202.21
2011/0036346 A1 2/2011 Cohen et al.
2011/0159705 A1 6/2011 Schmidt
2011/0192397 A1 8/2011 Saskar et al.
2011/0226266 A1 9/2011 Tao
2011/0265806 A1 11/2011 Alarcon et al.
2011/0277761 A1 11/2011 Terry et al.
2011/0278189 A1 11/2011 Terry et al.
2011/0303231 A1* 12/2011 Li ..... A24F 47/008 131/329
2012/0018529 A1 1/2012 Gammon et al.
2012/0048266 A1 3/2012 Alelov
2012/0111347 A1* 5/2012 Hon ..... A24F 40/42 131/329
2012/0174914 A1 7/2012 Pirshafiey et al.
2012/0199146 A1 8/2012 Marangos
2012/0199663 A1 8/2012 Qiu
2012/0223673 A1 9/2012 Chen et al.
2012/0255546 A1 10/2012 Goetz et al.
2012/0312313 A1 12/2012 Frija
2012/0318882 A1 12/2012 Abehasera
2012/0325227 A1 12/2012 Robinson et al.
2013/0056013 A1 3/2013 Terry et al.
2013/0081642 A1* 4/2013 Safari ..... A24F 47/008 131/329
2013/0174842 A1 7/2013 Young et al.
2013/0220315 A1 8/2013 Conley et al.
2013/0253433 A1 9/2013 Senior et al.
2013/0306084 A1 11/2013 Flick
2013/0319435 A1 12/2013 Flick
2014/0060554 A1* 3/2014 Collett ..... A24F 47/008 131/328
2014/0158129 A1 6/2014 Pratt, Jr. et al.
2014/0209105 A1* 7/2014 Sears ..... A24F 47/008 131/328
2014/0283859 A1 9/2014 Minskoff et al.
2017/0197046 A1 7/2017 Buchberger

FOREIGN PATENT DOCUMENTS

CA 2641869 A1 5/2010
CA 2884987 A1 * 8/2010 ..... A24F 47/008
CN 201104488 Y 8/2008
CN 101606758 * 12/2009 ..... A24F 47/008
CN 201379072 Y 1/2010
CN 201408820 Y 2/2010
CN 201430916 Y 3/2010
CN WO 2010091593 A1 * 8/2010 ..... A24F 47/008
CN 101869356 A 10/2010
CN 201781984 U 4/2011
CN 202004499 U 10/2011
CN 102727969 B 2/2014
DE 19619536 A1 10/1997
DE 102006004484 A1 8/2007
EP 0358114 A2 3/1990
EP 0845220 B1 9/2003
EP 2399636 A1 12/2011
GB 2264237 A 8/1993
GB 2266466 A 11/1993
KR 101011453 B1 1/2011
KR 20110006928 U 7/2011
KR 20120113519 A 10/2012
KR 20120008751 U 12/2012

(56) References Cited

FOREIGN PATENT DOCUMENTS

| | | | |
|---|---|---|---|
| WO | WO-2003061716 | A1 | 7/2003 |
| WO | WO-03103387 | A2 | 12/2003 |
| WO | WO-2004080216 | A1 | 9/2004 |
| WO | WO-2008077271 | A1 | 7/2008 |
| WO | WO-2010091593 | A1 | 8/2010 |
| WO | WO-2010118644 | A1 | 10/2010 |
| WO | WO-2011125058 | A1 | 10/2011 |
| WO | WO-2012059726 | A2 | 5/2012 |
| WO | WO-2012062600 | A1 | 5/2012 |
| WO | WO-2012173322 | A1 | 12/2012 |

* cited by examiner

Fig. 2c
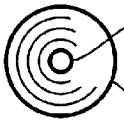
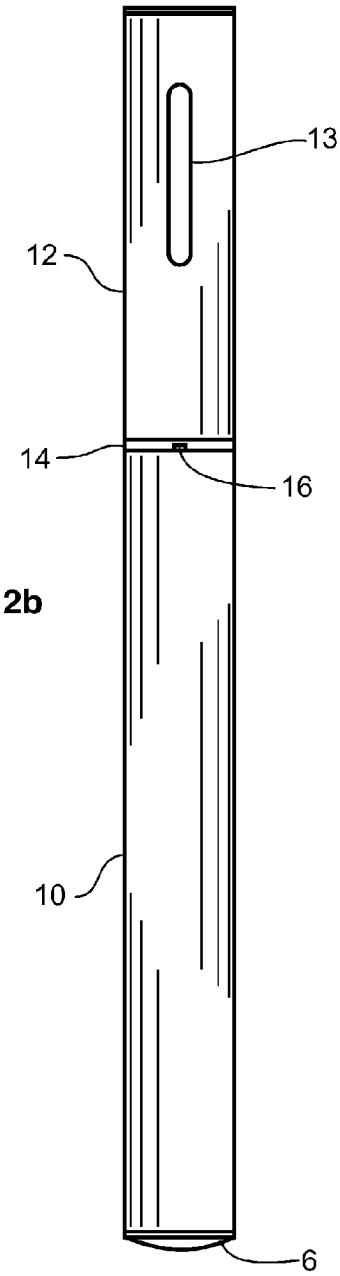
Fig. 2b
Fig. 2a
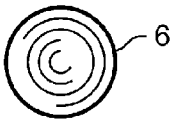
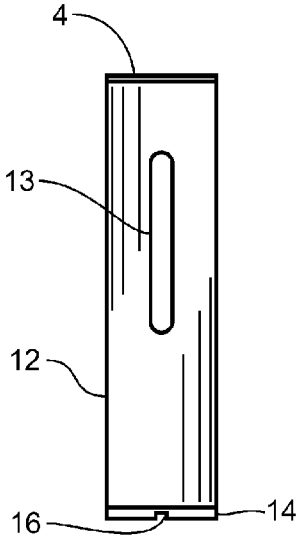
Fig. 3b
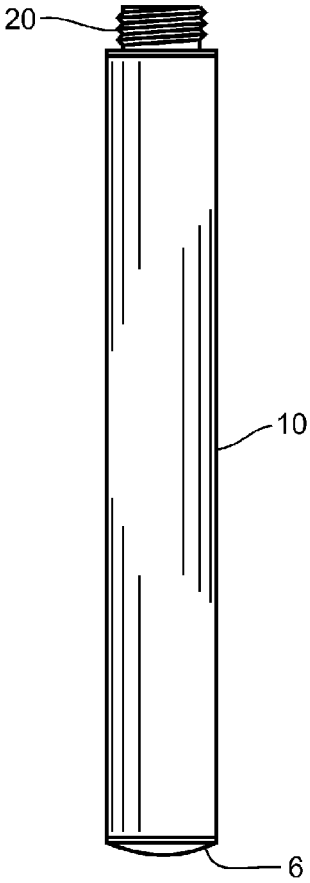
Fig. 3a

ELECTRONIC CIGARETTE WITH LIQUID RESERVOIR

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

Field of the Invention

The present invention relates to electronic cigarettes. More specifically, the present invention relates to an electronic cigarette with an internal liquid reservoir.

Description of the Related Art

Electronic cigarettes have become increasingly popular in recent times. Electronic cigarettes emulate a tobacco cigarettes, but without the combustion of tobacco during use. Rather than burning tobacco, a liquid is atomized within the electronic cigarette, which emulates the smoke produced in a tobacco cigarette. The liquid may contain flavoring agents such as tobacco flavor, menthol, and others, to enhance the "smoking" experience of the electronic cigarette. Nicotine has been added to the atomization liquid in prior art electronic cigarettes. In certain prior art electronic cigarettes, a reserve of liquid is stored within the cigarette housing in a porous material, which is placed into contact with an atomizing assembly such that the liquid can be gradually transferred to the atomizing assembly during consumption. A replaceable cartridge with a liquid soaked porous material has been provided to enable consumers to replenish the supply of liquid as it is depleted during use by replacing the cartridge. It should be appreciated that the structural and electrical components in an electronic cigarette are durable and outlast, by a long measure, the period of consumption for the quantity of liquid provided in such a porous reservoir.

Consumers of electronic cigarettes are experienced at replacing the liquid reservoir cartridges as the liquid is depleted during consumption. In fact, it is common for consumers to carry spare cartridges so that they are readily available in the event their current cartridge becomes depleted. In fact, this arrangement can become somewhat tedious after a period of use, and there is a general desire on the marketplace to extend the duration of use between cartridge changes, or even the elimination of the need to ever change cartridges. Thus is can be appreciated that there is a need in the art for an apparatus for increasing the quantity of liquid stored within an electronic cigarette and other means to reduce the frequency of replacing or adding additional liquid during use.

SUMMARY OF THE INVENTION

The need in the art is addressed by the apparatus of the present invention. The present invention teaches an electronic cigarette apparatus including an elongated housing that has a mouthpiece with an aerosol outlet, and an atomizer disposed within an atomizing chamber. The atomizer selectively generates an aerosol of the liquid in response to suction pressure at the aerosol outlet. The atomizing chamber has an air inlet, an atomizer outlet coupled to the aerosol outlet, and a first wick aperture. A liquid reservoir is disposed within the elongated housing, which is sealably separated from the atomizing chamber. A wick disposed through the first wick aperture between the liquid reservoir and the atomizing chamber and it is configured to transfer the liquid by capillarity from the liquid reservoir to the atomizer.

In a specific embodiment, the foregoing apparatus further includes an inlet vent formed on the exterior of the elongated housing that is coupled to deliver air to the atomizing chamber air inlet. In a refinement to this embodiment, the inlet vent is coupled to the atomizing chamber air inlet by a conduit. In a further refinement, the conduit sealably passes through the liquid reservoir.

In a specific embodiment of the foregoing apparatus, the atomizer outlet and the aerosol outlet are coupled together by a chimney. In a refinement to this embodiment, the chimney sealably passes through the liquid reservoir.

In a specific embodiment of the foregoing apparatus, the atomizer is a resistive heating element. In a refinement to this embodiment, the wick is partially engages the resistive heating element.

In a specific embodiment of the foregoing apparatus, the atomizer has a tubular form defining an open central passage. In a refinement to this embodiment, the wick passes through the open central passage.

In a specific embodiment of the foregoing apparatus, the atomizing chamber further includes a second wick aperture, and the apparatus is arranged such that a first end of the wick passes through the first wick aperture and a second end of the wick passes through the second wick aperture.

In a specific embodiment of the foregoing apparatus, the wick is fabricated as a bundle of heat resistant fibers. In a refinement to this embodiment, the bundle of heat resistant fibers is fiberglass. In another refinement to this embodiment, the bundle of heat resistant fibers is fabricated from a material selected from; aramid, fluorocarbon, sulfide, melamine, polyimide, carbon, and glass.

In a specific embodiment of the foregoing apparatus, the liquid reservoir is formed as an annular cavity between the interior of the elongated housing and the atomizing chamber. In another specific embodiment of the foregoing apparatus, the liquid reservoir includes an external access opening, for enabling addition of liquid into the liquid reservoir. In a refinement to this embodiment, the external access opening is a removable mouthpiece.

BRIEF DESCRIPTION OF THE DRAWINGS

FIGS. 2a, 2b, and 2c are a tip end view, a side view, and mouthpiece end view, respectively, drawings of an electronic cigarette according to an illustrative embodiment of the present invention.

FIGS. 3a and 3b are side view drawings, respectively, of a cartridge portion and a power supply portion of an electronic cigarette according to an illustrative embodiment of the present invention.

DESCRIPTION OF THE INVENTION

Figure 1:
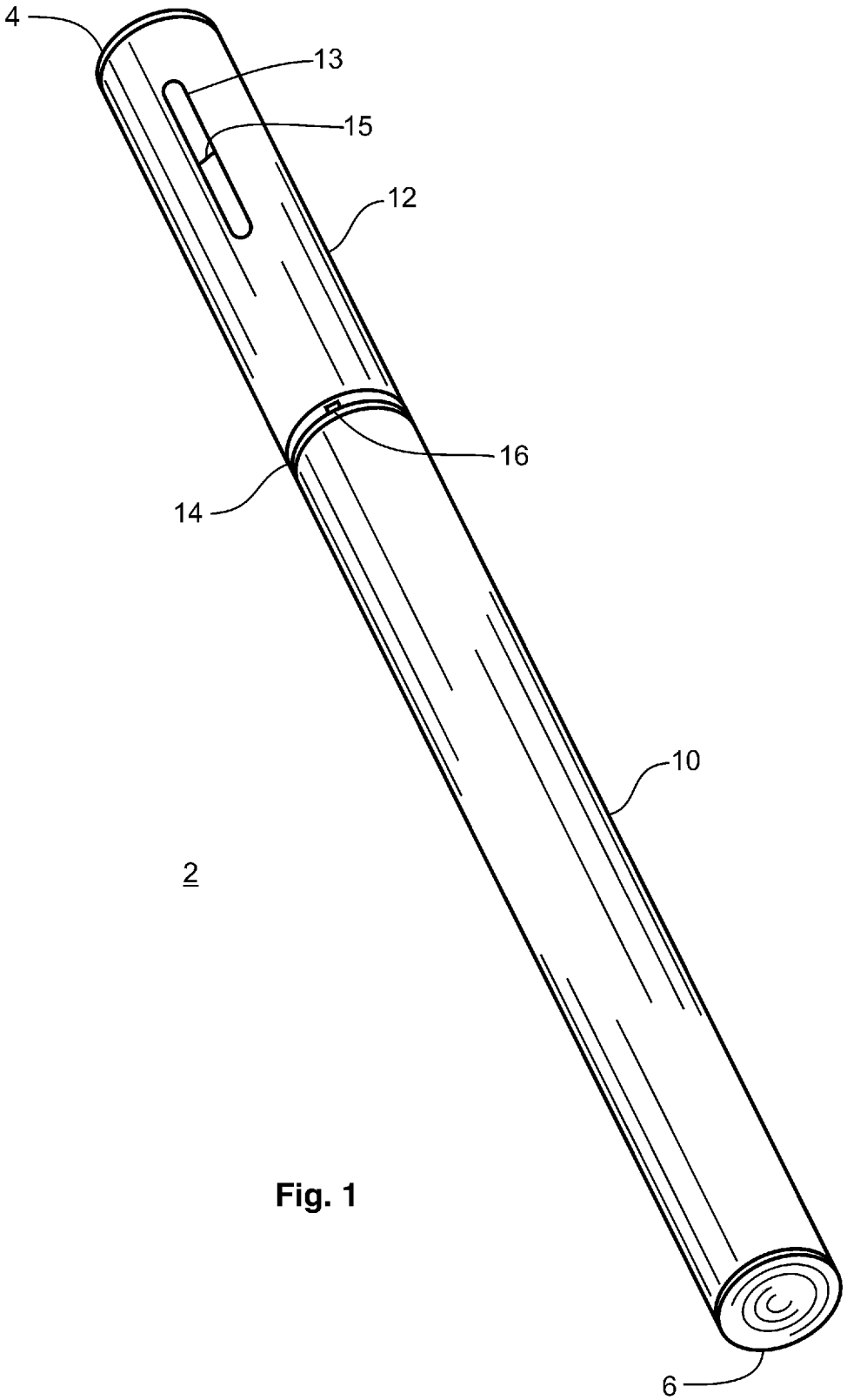
FIG. 1 is a perspective view drawing of an electronic cigarette according to an illustrative embodiment of the present invention.

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope hereof and additional fields in which the present invention would be of significant utility.

In considering the detailed embodiments of the present invention, it will be observed that the present invention resides primarily in combinations of steps to accomplish various methods or components to form various apparatus and systems. Accordingly, the apparatus and system components and method steps have been represented where appropriate by conventional symbols in the drawings, showing only those specific details that are pertinent to understanding the present invention so as not to obscure the disclosure with details that will be readily apparent to those of ordinary skill in the art having the benefit of the disclosures contained herein.

In this disclosure, relational terms such as first and second, top and bottom, upper and lower, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a" does not, without more constraints, preclude the existence of additional identical elements in the process, method, article, or apparatus that comprises the element.

The present invention advances the art of electronic cigarettes by teaching an electronic cigarette that provides a liquid reservoir, which effectively delivers liquid at the requisite rates from the reservoir to an atomizer in a open atomizing chamber. This arrangement enables production of aerosol of the liquid at desired rates of atomization without excessive liquid transfer during periods of non-use. This function is enabled though utilization of a wick aperture through the atomizing chamber and a wick disposed between the liquid reservoir and the atomizer. The wick enables the transfer of liquid by capillarity in a controlled manner without flooding the open atomization chamber.

Reference is directed to FIG. 1 is a perspective view drawing of an electronic cigarette 2 according to an illustrative embodiment of the present invention. The electronic cigarette 2 comprises a housing having a first elongated portion 10 and a second elongated portion 12. The second elongated portion 12, also referred to as the "cartridge" in certain illustrative embodiments, comprises a mouthpiece end 4, which has an aerosol outlet (not shown) for drawing air through the cartridge 12. The first elongated portion 10 and the second elongated portion 12 are removable joined together with a mechanical coupler 14. One or more air inlet vents 16 are provided about the coupler 14 for allowing airflow into the cartridge 12 when the user draws air through the electronic cigarette 2. The first elongated portion 10 comprises a tip end 6, which in the illustrative embodiment, is fabricated from a translucent material enabling the transmission of light therethrough. Within the second elongated portion 12 is disposed a liquid reservoir (not fully shown). The liquid reservoir includes a clear or translucent window 13 to the exterior of the housing 12 for visually determining the liquid level 15 within the liquid reservoir.

Now, considering FIGS. 2a, 2b, and 2c, these are a tip end view, a side view, and mouthpiece end view, respectively, drawing of an electronic cigarette according to an illustrative embodiment of the present invention. Note that the first elongated portion 10 and second elongated portion 12 combine at coupler 14 to present a complete electronic cigarette 2 that closely resembles a tobacco cigarette. The cartridge 12 is fabricated with a finished material resembling the filter of a tobacco cigarette, and the first elongated portion 10 is fabricated to resemble the tobacco roll of a tobacco cigarette. As noted above, the cartridge 12 includes a window 13 for visually determining the liquid level of the internal liquid reservoir (not shown). The mouthpiece end 4 includes an aerosol outlet opening 5, for drawing air and aerosol out of the cartridge 12. Air is inlet to the electronic cigarette 2 at the vent openings 16 located at the coupler 14. The air inlet openings 16 can be located elsewhere on the electronic cigarette 2, and is a matter of design choice. In the illustrative embodiment, the tip end 6 is a translucent gray material resembling an ash.

Reference is directed to FIGS. 3a and 3b, which are side view drawings, respectively, of a cartridge portion 12 and a power supply portion 10 of an electronic cigarette according to an illustrative embodiment of the present invention. A threaded extension 20 on the power supply portion 10 of the housing threadably engages the mechanical coupler 14 on the cartridge portion 12. In addition, as will be described more fully hereinafter, an electrical connection is also facilitated in the connection between the threaded extension 20 and the mechanical coupler 14. The cartridge portion 12 can thusly be installed, uninstalled, and replaced as needed. The cartridge portion contains the liquid reservoir and the window 13 provides the visual cue as to the liquid remaining The tip end 4 can be removed in certain illustrative embodiments to facilitate the addition of liquid to the reservoir. The tip end 6 glow by light of an internal amber LED in response to suction pressure at the aerosol outlet 5.

Figure 4C:
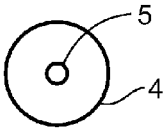
FIGS. 4a, 4b, and 4c are tip end view, side section view, and mouthpiece end view, respectively, drawings of an electronic cigarette according to an illustrative embodiment of the present invention.
Figure 4B:
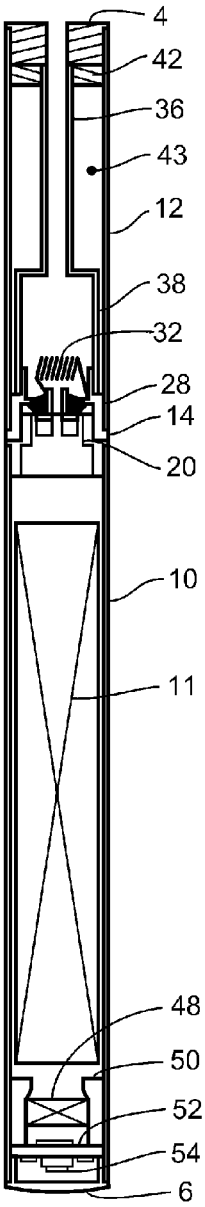
Figure 4A:
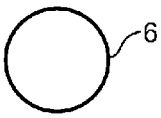
Figure 5B:
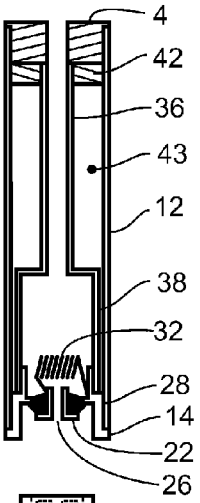
FIGS. 5a and 5b are side section view drawings, respectively, of a cartridge portion and a power supply portion of an electronic cigarette according to an illustrative embodiment of the present invention.
Figure 5A:
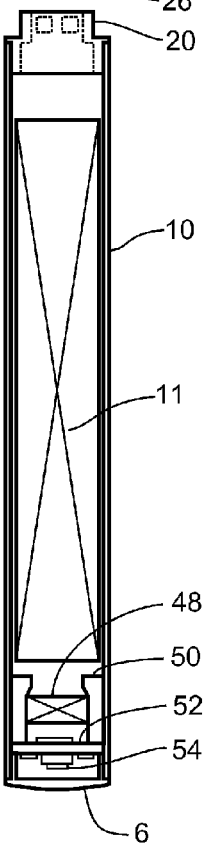

Reference is directed to FIGS. 4a, 4b, and 4c, which are tip end view, side section view, and mouthpiece end view, respectively, drawings of an electronic cigarette according to an illustrative embodiment of the present invention. Reference is additionally directed to FIGS. 5a and 5b, which are side section view drawings, respectively, of a cartridge portion and a power supply portion of an electronic cigarette correspond to this illustrative embodiment. FIGS. 4 and 5 correspond to the same illustrative embodiment and provide details of the internal structures of the illustrative embodiment. The tip end 4 is a resilient insert that engages the interior of the cartridge housing 12 and provides the aerosol outlet 5, which is a passage formed therethrough. Within the cartridge housing 12 is an atomizing chamber 38 that has an open chimney 36 extending to the aerosol outlet 5. The chimney 36 is located within the cartridge housing by a resilient seal 42. The annular space formed between the interior of the cartridge housing 12 and the chimney 36 defines the liquid reservoir 43. At the upper end, resilient seal 42 closes and seals the liquid reservoir 43. The lower end of the reservoir 43 engages the atomizer assembly 28, which will be more fully described hereinafter.

In FIGS. 4 and 5, the atomizer assembly 28 include the atomizer 32, which is disposed within the atomizer chamber 38. In addition, the atomizer assembly 28 comprises the mechanical coupler 14 that engages the threaded extension 20 of the power supply portion 10. Within the mechanical coupler 14, and also a part of the atomizer assembly 28, is an electrical coupler 22 that has an air inlet port 26 formed therethrough, which is pneumatically coupled into the atomizing chamber 38. Thusly, the pathway for the flow of fresh air in and aerosol out includes air drawn through the mechanical coupler 14, through the air inlet port 26, to the atomizer 32 within the atomizing chamber 38, up the chimney 36 and out the aerosol outlet 5.

In FIGS. 4 and 5, the power supply portion 10 of the housing has a threaded extension 20 that engages the mechanical coupler 14. There is also a corresponding electrical connection such that the power supply portion 10 can deliver electric current to the atomizer 32 to facilitate generation of aerosol. Two conductors are provided, including the outer mechanical connection and the central pneumatic/electric connection. Suitable milling for air-flow channels is provided to facilitate solid mechanical, conductive electrical, and pneumatic connections. In the illustrative embodiment, power is derived from a storage battery 11. A pressure sensor 48 detects negative pressure within the housing 10 and energizes the atomizer. The pressure sensor 46 is located by a pressure seal 50. A draw circuit 52 provides the electrical operation functions. In addition, and amber LED 54 is disposed to illuminate through the translucent tip 6 to emulate burning ash while the draw pressure sensor 48 detects negative pressure.

Figure 6:
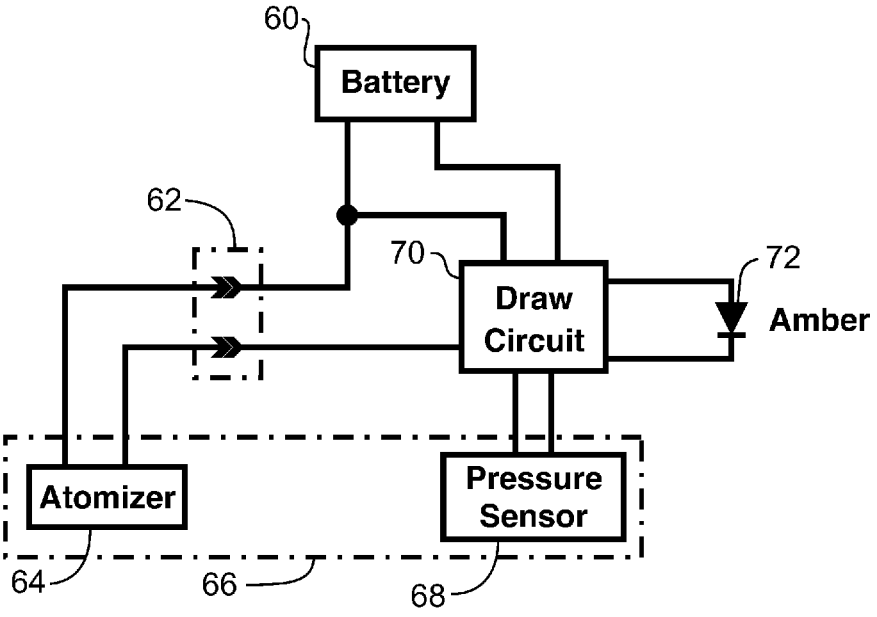
FIG. 6 is a functional block diagram an electronic cigarette according to an illustrative embodiment of the present invention.

Reference is directed to FIG. 6, which is a functional block diagram an electronic cigarette according to an illustrative embodiment of the present invention. This diagram presents the electrical functions of the electronic cigarette. The battery 60 provides power to a draw circuit 70. A pressure sensor 68 is disposed within the cigarette housing 68. When negative pressure is detected, the draw circuit 70 delivers electric power to the atomizer 64 and the amber LED 72. This action causes aerosol to be produced in the presence of the negative pressure, and the tip of the electronic cigarette to glow amber so long as the negative pressure continues. The atomizer 64 is electrically coupled to the circuit through electrical coupler 62.

Figure 7:
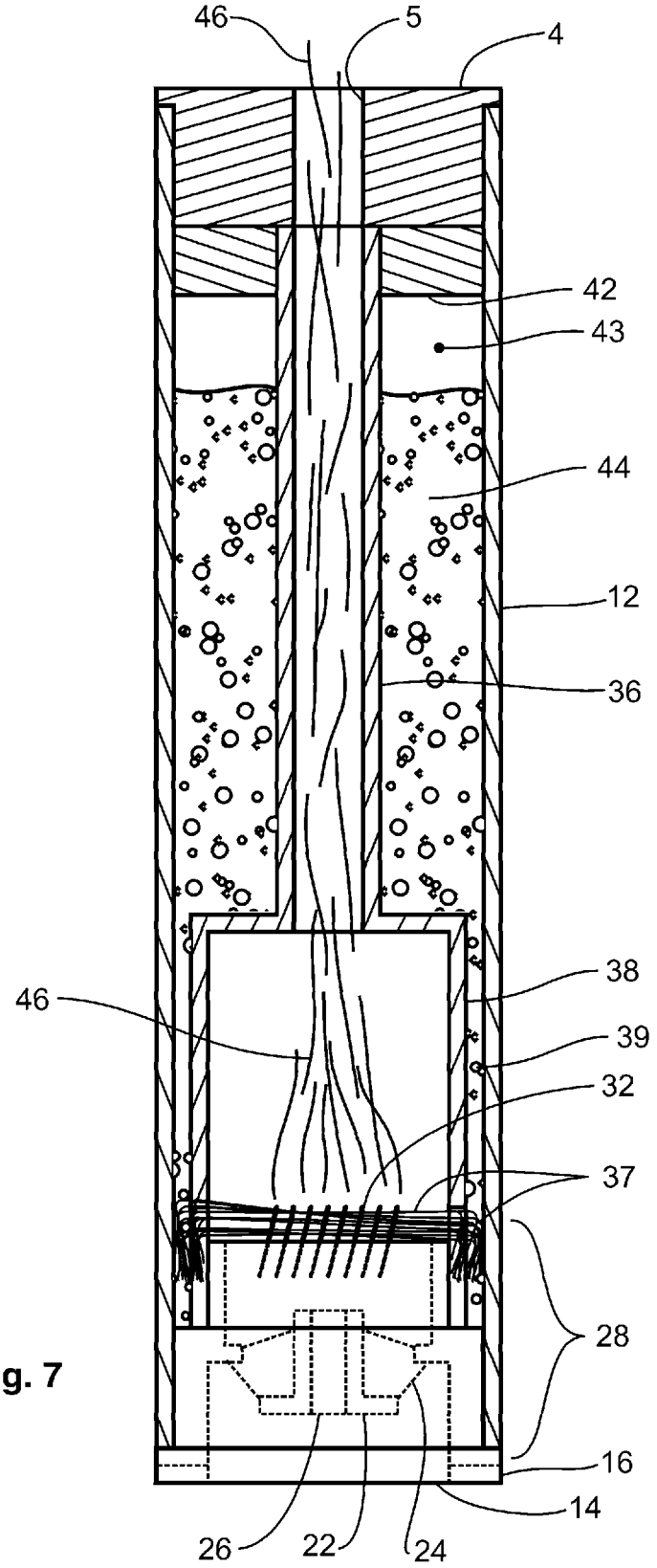
FIG. 7 is a detailed side section view drawing of a liquid reservoir cartridge according to an illustrative embodiment of the present invention.

Reference is directed to FIG. 7, which is a detailed side section view drawing of a liquid reservoir cartridge according to an illustrative embodiment of the present invention. This drawing provides further details into the structure and operation of the liquid reservoir cartridge assembly. The cartridge comprises an outer housing 12 that is closed at the upper end by the tip end resilient insert 4, which has the aerosol port 5 formed therethrough. The lower end of the housing 12 is closed with the atomizer assembly 28, which has the mechanical coupler 14 at the extreme end. Plural air inlet vents 16 are formed though the mechanical coupler so that fresh air can enter while it is secured to the power supply housing. Within the cartridge housing 12 is the atomizing chamber 38 that is pneumatically coupled to the chimney 36, which is aligned with the aerosol outlet 5. The chimney 36 is located and sealed at the upper end by resilient seal 42. The annular space 43 between the chimney 36 and the interior of the housing 12 defines the liquid reservoir 43. Note that there is a thinner annular cavity 39 formed between the exterior of the atomizing chamber 38 and interior of the cartridge housing 12. The fluid 44 is stored in the fluid reservoir 43, and is also capable of flowing into the annular cavity 39 to saturate wick 37.

In FIG. 7, the atomizing assembly 28 is comprised of several components. The atomizer 32 is a coiled nickel-chromium heater through which the wick 37 passes. The wick 37 passes through wick apertures in the atomizing chamber (not shown) on its two ends, and into the annular cavity 39. The atomizer assembly 28 is machined from a suitable metal and includes the mechanical couple 14, the electrical coupler 22, which is supported by an insulative support 24, and which has the air inlet port 26 formed therethrough. During operation, when there is a negative pressure imposed on the system by drawing air out of the aerosol outlet 5, and while electric current is delivered to the atomizer 36, air enters the air inlet port 26 and carries aerosol of the liquid 46 away from the atomizer 32, up the chimney 36 and out the aerosol outlet 5. As the liquid in the wick 37 is depleted by the atomizer 32, capillary action draws additional liquid from the liquid reservoir 43, through the cavity 39 and to the atomizer 32.

Figure 8:
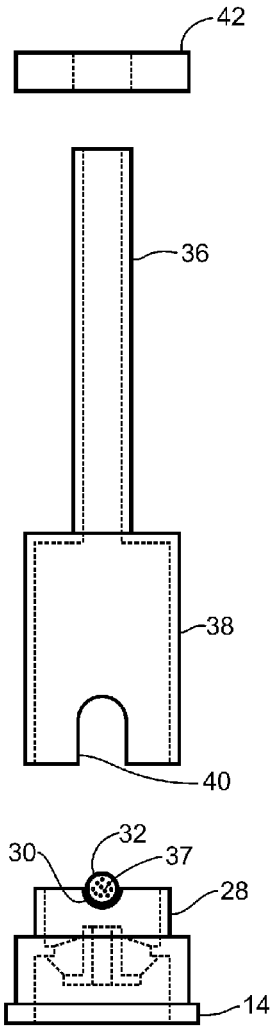
FIG. 8 is an exploded view drawing of a liquid reservoir cartridge according to an illustrative embodiment of the present invention.

Reference is directed to FIG. 8, which is an exploded view drawing of an atomizer 28, atomizing chamber 38, chimney 36 and resilient seal 42 according to an illustrative embodiment of the present invention. In the illustrative embodiment, the atomizing chamber 38 and chimney 36 are formed as a single unit. The resilient seal 42 is a donut shaped polymeric material that is pressed onto the upper end of the chimney 36. The atomizing chamber 38 includes a pair of opposing wick apertures 40 formed therein, which provide clearance for the wick 37 to pass into the atomizing chamber 38. The atomizing assembly 28 includes the mechanical coupler 14 at its lower end and the atomizer 32 at its upper end. The wick 37 passes through the center of the atomizer 32. The atomizing assembly has a pair of semicircular recesses 30 formed therein which align cooperatively with the wick apertures 40 in the atomizing chamber when the two units are engaged. This results in a circular aperture through which the wick 37 passes with a slightly compressive fit. This arrangement enables liquid to pass through by capillarity of the wick 37, but prevents the liquid from flooding the atomizing chamber 38, which would be detrimental or atomizer function.

Figure 9:
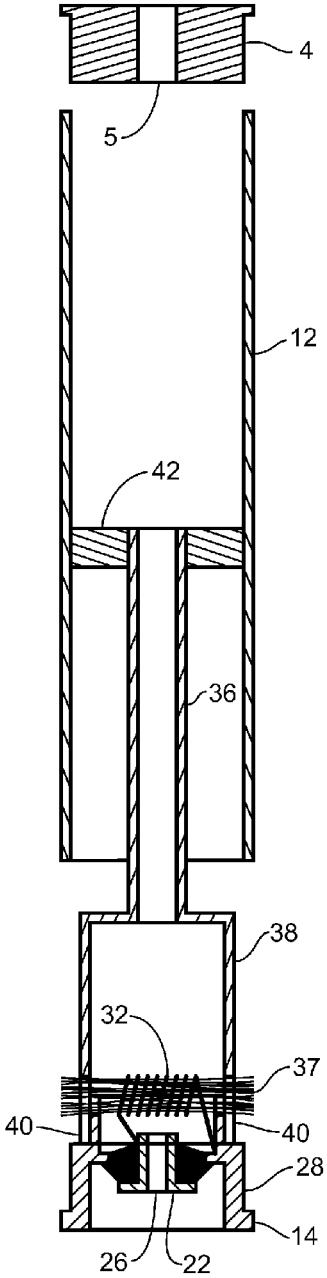
FIG. 9 is a partially exploded section view drawing of a liquid reservoir cartridge according to an illustrative embodiment of the present invention.
Figure 10:
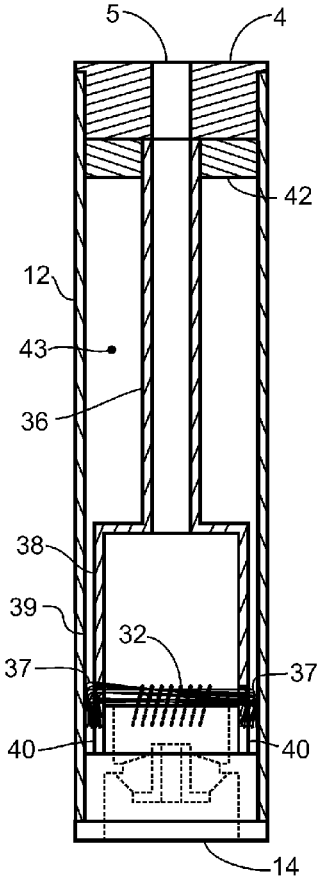
FIG. 10 is a section view drawing of a liquid reservoir cartridge according to an illustrative embodiment of the present invention.
Figure 11D:
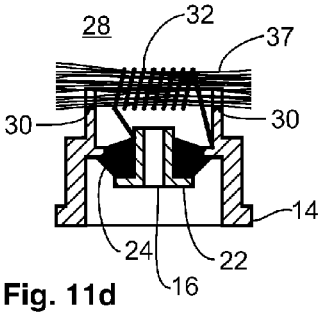
FIG. 11a, 11b, 11c, and 11d are a first end view, a first side section view, a second end view, and a second side section view drawing, respectively, of an atomizing assembly according to an illustrative embodiment of the present invention.
Figure 11C:
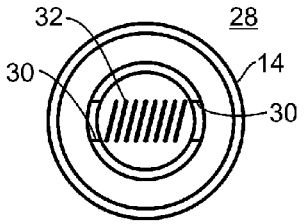
Figure 11B:
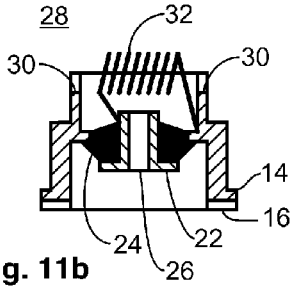
Figure 11A:
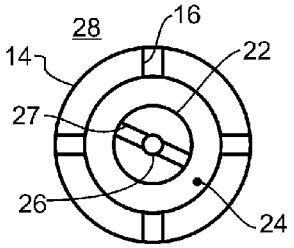

Reference is directed to FIG. 9, which is a partially exploded side section view drawing, and to FIG. 10, which is an assembled side section view drawing, of a liquid reservoir cartridge according to an illustrative embodiment of the present invention. The wick 37 passes through the atomizer 32 and extends to the outer periphery of the atomizer assembly 28. The atomizing chamber 38 is engaged with the atomizing assembly 28, thereby perfecting the wick aperture 40 as described hereinbefore, and enclosing the atomizing chamber 38. The resilient seal 42 is disposed between the exterior of the chimney 36 and the interior of the housing 12, thereby sealing the upper end of the fluid reservoir 43. The tip end resilient insert 4, with the aerosol outlet port 5, closes the upper end of the cartridge housing 12, and the chimney 36 is thereby aligned and sealed to the aerosol outlet 5. The housing 12 is engaged with the atomizer assembly 28, which urges the ends of the wick 37 downwardly and constrains them within the annular cavity 39 formed between the interior of the housing 12 and the exterior of the atomizing chamber 38. The wick 37 is thusly enabled to absorb the liquid (not shown). The atomizer 32 has a first end electrically coupled to the atomizer assembly body 28 and a second end electrically coupled to the electrical coupler 22. The electrical circuit is completed when the cartridge is engaged with the power supply portion, discussed hereinbefore. The atomizing chamber 38 is thusly sealed but for the entry of fresh air through air inlet port 26 and the exit of air and aerosol up chimney 36 and out aerosol outlet 5.

Reference is directed to FIGS. 11a, 11b, 11c, and 11d, which are a first end view, a first side section view, a second end view, and a second side section view drawing, respectively, of an atomizing assembly 28 according to an illustrative embodiment of the present invention. The assembly is based on a metal body 28 that has a electrical coupler 22 insulatively supported 24 therein. The electrical coupler 22 has an air inlet port formed therethrough. The electrical coupler has a pair of air recesses 27 machined on its face so that an air channel is created when the cartridge is engaged with the power supply portion of the electronic cigarette. In this manner, the air path is from the exterior, through the air inlet vents 16, through the air recesses 27, through the air inlet port 26 of the electrical coupler and u to the atomizer 32. The wick 37 is positioned through the central cavity of the atomizer 32 and extends through the pair of semicircular recesses 30 in the body 28. The wick is a fibrous bundle, which is formed from a temperature resistant material, and may be selected from amongst aramid, fluorocarbon, sulfide, melamine, polyimide, carbon, and glass fibers. Or, from other suitable materials known to those skilled in the art.

Figure 12C:
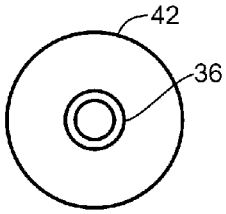
FIGS. 12a, 12b, and 12c are a first end view, a side section view, and a second end view drawing, respectively, of an atomizing chamber according to an illustrative embodiment of the present invention.
Figure 12B:
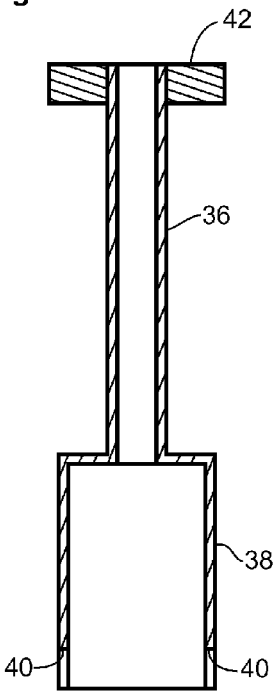
Figure 12A:
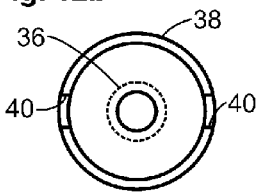

Reference is directed to FIGS. 12a, 12b, and 12c, which are a first end view, a side section view, and a second end view drawing, respectively, of an atomizing chamber 38 and chimney 6 according to an illustrative embodiment of the present invention. In the illustrative embodiment, the atomizing chamber 38 and chimney 36 are formed as a single unit. The atomizing chamber 38 and the chimney 36 are cylindrical in form. The resilient seal 42 is a donut shaped polymeric material that is pressed onto the upper end of the chimney 36. The atomizing chamber 38 includes a pair of opposing wick apertures 40 formed therein, which provide clearance for the wick (not shown) to pass into the atomizing chamber 38.

Figure 13C:
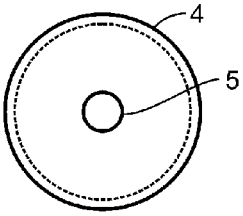
FIGS. 13a, 13b, and 13c are a first end view, a side section view, and a second end view drawing, respectively, of a mouthpiece housing according to an illustrative embodiment of the present invention.
Figure 13B:
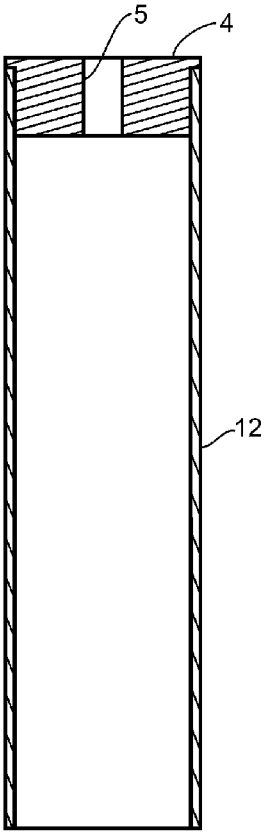
Figure 13A:
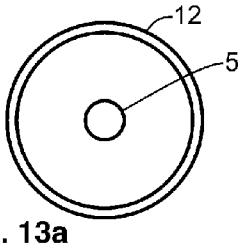

Reference is directed to FIGS. 13a, 13b, and 13c, which are a first end view, a side section view, and a second end view drawing, respectively, of a mouthpiece housing 12 according to an illustrative embodiment of the present invention. The housing 12 is a cylindrical plastic tube in the illustrative embodiment. The plastic is transparent or translucent to facilitate visual inspection of the liquid content. The tip end resilient insert 4, with the aerosol outlet port 5, closes the upper end of the cartridge housing 12.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. An electronic cigarette cartridge apparatus, comprising:
a housing having a mouthpiece with an aerosol outlet;
an atomizer disposed within an atomizing chamber, and operable to selectively generate an aerosol of [the] *a* liquid in response to electric current flowing therethrough;
said atomizing chamber having an air inlet, an atomizer outlet coupled to said aerosol outlet, [and] a first wick aperture*, and a second wick aperture*;
a liquid reservoir disposed within said housing and sealably separated from said atomizing chamber[.]*;* and
a wick [disposed] *in contact with the liquid in the liquid reservoir* through said first wick aperture [between said liquid reservoir and said atomizing chamber] and *said second wick aperture, the wick disposed between the liquid reservoir and the atomizer and* configured to transfer the liquid by capillarity from said liquid reservoir to said atomizer;
wherein said atomizer outlet and said aerosol outlet are coupled by a chimney.

2. The apparatus of claim 1, further comprising:
an inlet vent formed on the exterior of said housing and coupled to deliver air to said atomizing chamber air inlet.

3. The apparatus of claim 2, [and] wherein said inlet vent is coupled to said atomizing chamber air inlet by a conduit.

4. The apparatus of claim 3, [and] wherein said conduit sealably passes through said liquid reservoir.

5. The apparatus of claim 1, [and] wherein said chimney sealably passes through said liquid reservoir.

6. The apparatus of claim 1, [and] wherein said atomizer is a resistive heating element.

7. The apparatus of claim 6, [and] wherein said wick [is] partially engages said resistive heating element.

8. The apparatus of claim 1, [and] wherein said atomizer has a tubular form defining an open central passage.

9. The apparatus of claim 8, [and] wherein said wick passes through said open central passage.

10. The apparatus of claim 1, [and] wherein [said atomizing chamber further comprises a second wick aperture, and wherein] a first end of said wick passes through said first wick aperture and a second end of said wick passes through said second wick aperture.

[11. The apparatus of claim 1, and wherein said wick is fabricated as a bundle of heat resistant fibers.]

12. The apparatus of claim [11] *1*, [and] *wherein said wick comprises a bundle of heat resistant fibers, and* wherein said bundle of heat resistant fibers is fiberglass.

13. The apparatus of claim [11] *1*, [and] *wherein said wick comprises a bundle of heat resistant fibers, and* wherein said bundle of heat resistant fibers is fabricated from a material selected from; aramid, fluorocarbon, sulfide, melamine, polyimide, carbon, and glass.

14. The apparatus of claim 1, [and] wherein said liquid reservoir is formed as an annular cavity between [the] *an* interior of said housing and said atomizing chamber.

15. The apparatus of claim 1, [and] wherein said liquid reservoir includes an external access opening[, ] for enabling addition of liquid into said liquid reservoir.

16. The apparatus of claim 15, [and] wherein said external access opening is a removable mouthpiece.

*17. A method, comprising:*

*transferring liquid from a liquid reservoir of an electronic cigarette cartridge to an atomizing chamber of the cartridge with a wick extending between the liquid reservoir and the atomizing chamber, wherein the liquid reservoir surrounds and is sealed from an interior of the atomizing chamber;*

*generating an aerosol of the liquid in the atomizing chamber; and*

*channeling the aerosol from an outlet of the atomizing chamber to an aerosol outlet of the electronic cigarette cartridge with a chimney coupled to the outlet of the atomizing chamber and to the aerosol outlet.*

*18. The method of claim 17, where the liquid reservoir is without a porous material for storing the liquid.*

*19. The method of claim 17, wherein transferring liquid from a liquid reservoir to an atomizing chamber with a wick comprises transferring the liquid by capillarity with the wick.*

*20. The method of claim 17, wherein generating an aerosol of the liquid comprises generating aerosol with an electrically powered atomizer in the atomizing chamber.*

*21. The method of claim 17, wherein channeling the aerosol with a chimney comprises channeling the aerosol with the chimney through the liquid reservoir, the chimney being sealed from the liquid reservoir.*

*22. The apparatus of claim 1, wherein the wick extends between the liquid reservoir and an interior of the atomizing chamber.*

*23. The apparatus of claim 1, wherein the liquid reservoir adjacent the wick is free from porous material.*

*24. The apparatus of claim 1, wherein the first wick aperture is circular.*

*25. The apparatus of claim 1, further comprising an atomizing assembly comprising a body and the atomizer, the atomizing assembly comprising a first recess formed therein that aligns with the first wick aperture in the atomizing chamber and provides a compressive fit around the wick.*

*26. The apparatus of claim 25, wherein the first wick aperture and the first recess cooperate to define a circular aperture.*

*27. The apparatus of claim 10, wherein the first wick aperture and the second wick aperture each comprise a fixed width slot terminating in a curved end, the fixed width configured to receive the wick.*

*28. The apparatus of claim 1, wherein the liquid reservoir surrounds and is sealed from an interior of the atomizing chamber.*

*29. The apparatus of claim 1, wherein the chimney is sealed to the atomizer outlet.*

*30. The apparatus of claim 1, wherein the apparatus comprises a sealed path from the atomizer outlet, through the chimney to the aerosol outlet.*

*31. The apparatus of claim 1, wherein the chimney and atomizing chamber are cylindrical and the maximum exterior diameter of the chimney is less than the maximum interior diameter of the atomizing chamber.*

*32. The apparatus of claim 1, wherein the apparatus is elongate, and the maximum transverse exterior dimension of the chimney is less than the maximum transverse interior diameter of the atomizing chamber.*

*33. The apparatus of claim 1, wherein the atomizing chamber and the chimney are formed as a single unit.*

*34. The apparatus of claim 1, wherein the housing comprises a transparent material through which the liquid in the liquid reservoir can be viewed from the exterior of the apparatus.*

*35. The apparatus of claim 1, further comprising an insert in the housing, the insert comprising the aerosol outlet.*

*36. The apparatus of claim 1, coupled to a power supply portion, wherein the power supply portion comprises a pressure sensor configured to detect negative pressure within the power supply portion and energize the atomizer.*

*37. The apparatus of claim 36, wherein the power supply portion comprises an LED positioned at a tip end of the power supply portion, the LED configured to illuminate in response to the pressure sensor detecting negative pressure in the power supply portion.*

*38. The apparatus of claim 37, wherein the LED comprises an amber LED configured to emulate burning ash when illuminated.*

*39. The apparatus of claim 1, wherein the chimney is sealed to the atomizer outlet, the chimney and atomizing chamber are cylindrical, and the apparatus comprises a sealed path from the atomizer outlet, through the chimney to the aerosol outlet.*

*40. The apparatus of claim 1, wherein the liquid reservoir surrounds and is sealed from an interior of the atomizing chamber, the atomizing chamber and the chimney are formed as a single unit, and the apparatus comprises a sealed path from the atomizer outlet, through the chimney to the aerosol outlet.*

*41. A cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture at opposite sides of the atomizing chamber;*

*a liquid reservoir at least partially defined by an interior of the cartridge housing and an exterior of the atomizing chamber, the liquid reservoir configured to contain an atomization liquid, the liquid reservoir comprising a clear or translucent window to an exterior of the cartridge housing, the clear or translucent window allowing visual determination of a liquid level within the liquid reservoir;*

*a chimney forming at least part of an aerosol outlet path sealably passing through the reservoir between the atomizer outlet and the aerosol outlet;*

*an atomizer disposed within the atomizing chamber, the atomizer comprising a resistive heating element; and*

*a wick in contact with the atomization liquid in the liquid reservoir through the first wick aperture and the second wick aperture, the wick disposed between the liquid reservoir and the atomizer.*

*42. An electronic cigarette comprising:*

*a power supply portion comprising a rechargeable battery; and*

*a cartridge configured for separable attachment to the power supply portion; the cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture at opposite sides of the atomizing chamber;*

*a liquid reservoir at least partially defined by an interior of the cartridge housing and an exterior of the atomizing chamber, the liquid reservoir configured to contain an atomization liquid, the liquid reservoir comprising a clear or translucent window to an exterior of the cartridge housing, the clear or translucent window allowing visual determination of a liquid level within the liquid reservoir;*

*a chimney forming at least part of an aerosol outlet path sealably passing through the reservoir between the atomizer outlet and the aerosol outlet;*

*an atomizer disposed within the atomizing chamber, the atomizer comprising a resistive heating element; and*

*a wick in contact with the atomization liquid in the liquid reservoir through the first wick aperture and the second wick aperture, the wick disposed between the liquid reservoir and the atomizer.*

*43. A cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture;*

*a liquid reservoir at least partially defined by an interior of the cartridge housing and an exterior of the atomizing chamber, the liquid reservoir configured to contain an atomization liquid;*

*a chimney forming at least part of an aerosol outlet path sealably passing through the reservoir between the atomizer outlet and the aerosol outlet;*

*an atomizer disposed within the atomizing chamber, the atomizer comprising a resistive heating element; and*

*a wick in contact with the atomization liquid in the liquid reservoir through the first wick aperture and the second wick aperture, the wick disposed between the liquid reservoir and the atomizer.*

*44. An electronic cigarette comprising:*

*a power supply portion comprising a rechargeable battery; and*

*a cartridge configured for separable attachment to the power supply portion; the cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture;*

*a liquid reservoir at least partially defined by an interior of the cartridge housing and an exterior of the atomizing chamber, the liquid reservoir configured to contain an atomization liquid;*

*a chimney forming at least part of an aerosol outlet path sealably passing through the reservoir between the atomizer outlet and the aerosol outlet;*

*an atomizer disposed within the atomizing chamber, the atomizer comprising a resistive heating element; and*

*a wick in contact with the atomization liquid in the liquid reservoir through the first wick aperture and the second wick aperture, the wick disposed between the liquid reservoir and the atomizer.*

*45. A cartridge comprising:*

*a mouthpiece end comprising an aerosol outlet;*

*an atomizing chamber comprising a first wick aperture and a second wick aperture each forming an opening between the atomizing chamber and a liquid reservoir configured to contain an atomization liquid; the atomizing chamber further comprising an atomizer outlet;*

*a wick partially disposed within the atomizing chamber, the wick having a first wick end extending out of the atomizing chamber through the first wick aperture into the liquid reservoir and a second wick end extending out of the atomizing chamber through the second wick aperture into the liquid reservoir, the wick configured to draw the atomization liquid into the atomizing chamber by capillarity; and*

*an atomizer disposed within the atomizing chamber, the atomizer configured to receive electric current from a battery to facilitate generation of an aerosol by vaporizing the atomization liquid drawn into the atomizing chamber by the wick;*

*wherein the atomizer outlet and the aerosol outlet are coupled by a chimney.*

*46. A cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture at opposite sides of the atomizing chamber;*

*a liquid reservoir at least partially defined by an interior of the cartridge housing and an exterior of the atomizing chamber, the liquid reservoir configured to contain an atomization liquid;*

*a chimney forming at least part of an aerosol outlet path sealably passing through the reservoir between the atomizer outlet and the aerosol outlet;*

*an atomizer disposed within the atomizing chamber, the atomizer comprising a resistive heating element; and*

*a wick in contact with the atomization liquid in the liquid reservoir through the first wick aperture and the second wick aperture, the wick disposed between the liquid reservoir and the atomizer.*

*47. An electronic cigarette comprising:*

*a power supply portion comprising a rechargeable battery; and*

*a cartridge configured for separable attachment to the power supply portion; the cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber*

*further comprising a first wick aperture and a second wick aperture at opposite sides of the atomizing chamber;*

*a liquid reservoir at least partially defined by an interior of the cartridge housing and an exterior of the atomizing chamber, the liquid reservoir configured to contain an atomization liquid;*

*a chimney forming at least part of an aerosol outlet path sealably passing through the reservoir between the atomizer outlet and the aerosol outlet;*

*an atomizer disposed within the atomizing chamber, the atomizer comprising a resistive heating element; and*

*a wick in contact with the atomization liquid in the liquid reservoir through the first wick aperture and the second wick aperture, the wick disposed between the liquid reservoir and the atomizer.*

*48. A cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture at opposite sides of the atomizing chamber;*

*a liquid reservoir at least partially defined by an interior of the cartridge housing and an exterior of the atomizing chamber, the liquid reservoir configured to contain an atomization liquid;*

*a chimney forming at least part of an aerosol outlet path sealably passing through the reservoir between the atomizer outlet and the aerosol outlet;*

*a resilient seal disposed between an exterior of the chimney and the interior of the cartridge housing, the resilient seal sealing an upper end of the liquid reservoir and locating the chimney within the cartridge housing;*

*an atomizer disposed within the atomizing chamber, the atomizer comprising a resistive heating element; and*

*a wick in contact with the atomization liquid in the liquid reservoir through the first wick aperture and the second wick aperture, the wick disposed between the liquid reservoir and the atomizer.*

*49. An electronic cigarette comprising:*

*a power supply portion comprising a rechargeable battery; and*

*a cartridge configured for separable attachment to the power supply portion; the cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture at opposite sides of the atomizing chamber;*

*a liquid reservoir at least partially defined by an interior of the cartridge housing and an exterior of the atomizing chamber, the liquid reservoir configured to contain an atomization liquid;*

*a chimney forming at least part of an aerosol outlet path sealably passing through the reservoir between the atomizer outlet and the aerosol outlet;*

*a resilient seal disposed between an exterior of the chimney and the interior of the cartridge housing, the resilient seal sealing an upper end of the liquid reservoir and locating the chimney within the cartridge housing;*

*an atomizer disposed within the atomizing chamber, the atomizer comprising a resistive heating element; and*

*a wick in contact with the atomization liquid in the liquid reservoir through the first wick aperture and the second wick aperture, the wick disposed between the liquid reservoir and the atomizer.*

*50. A cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture at opposite sides of the atomizing chamber;*

*a liquid reservoir at least partially defined by an interior of the cartridge housing and an exterior of the atomizing chamber, the liquid reservoir configured to contain an atomization liquid, the liquid reservoir comprising a clear or translucent window to an exterior of the cartridge housing, the clear or translucent window allowing visual determination of a liquid level within the liquid reservoir;*

*a chimney formed as a single unit with the atomizing chamber, the chimney forming at least part of an aerosol outlet path sealably passing through the liquid reservoir between the atomizer outlet and the aerosol outlet;*

*a resilient seal disposed between an exterior of the chimney and the interior of the cartridge housing, the resilient seal sealing an upper end of the liquid reservoir and locating the chimney within the cartridge housing;*

*an atomizer disposed within the atomizing chamber, the atomizer comprising a resistive heating element;*

*a wick in contact with the atomization liquid in the liquid reservoir through the first wick aperture and the second wick aperture, the wick disposed between the liquid reservoir and the atomizer, the wick comprising a first wick end passing through the first wick aperture and a second wick end passing through the second wick aperture; and*

*an atomizing assembly engaged with the atomizing chamber, the atomizing assembly having a pair of semicircular recesses formed therein, the pair of semicircular recesses aligning cooperatively with the first wick aperture and the second wick aperture of the atomizing chamber to result in a pair of circular apertures through which the first wick end and the second wick end pass with a compressive fit.*

*51. An electronic cigarette comprising:*

*a power supply portion comprising a rechargeable battery; and*

*a cartridge configured for separable attachment to the power supply portion; the cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an*

*atomizing chamber air inlet; the atomizing chamber further comprising a first wick aperture and a second wick aperture at opposite sides of the atomizing chamber;*

*a liquid reservoir at least partially defined by an interior of the cartridge housing and an exterior of the atomizing chamber, the liquid reservoir configured to contain an atomization liquid, the liquid reservoir comprising a clear or translucent window to an exterior of the cartridge housing, the clear or translucent window allowing visual determination of a liquid level within the liquid reservoir;*

*a chimney formed as a single unit with the atomizing chamber, the chimney forming at least part of an aerosol outlet path sealably passing through the liquid reservoir between the atomizer outlet and the aerosol outlet;*

*a resilient seal disposed between an exterior of the chimney and the interior of the cartridge housing, the resilient seal sealing an upper end of the liquid reservoir and locating the chimney within the cartridge housing;*

*an atomizer disposed within the atomizing chamber, the atomizer comprising a resistive heating element;*

*a wick in contact with the atomization liquid in the liquid reservoir through the first wick aperture and the second wick aperture, the wick disposed between the liquid reservoir and the atomizer, the wick comprising a first wick end passing through the first wick aperture and a second wick end passing through the second wick aperture; and*

*an atomizing assembly engaged with the atomizing chamber, the atomizing assembly having a pair of semicircular recesses formed therein, the pair of semicircular recesses aligning cooperatively with the first wick aperture and the second wick aperture of the atomizing chamber to result in a pair of circular apertures through which the first wick end and the second wick end pass with a compressive fit.*

*52. A cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture at opposite sides of the atomizing chamber, the atomizing chamber defining an open central passage;*

*a non-porous liquid reservoir at least partially defined by an interior of the cartridge housing and an exterior of the atomizing chamber, the liquid reservoir configured to contain an atomization liquid, the liquid reservoir comprising a clear or translucent window to an exterior of the cartridge housing, the clear or translucent window allowing visual determination of a liquid level within the liquid reservoir;*

*a chimney formed as a single unit with the atomizing chamber, the chimney forming at least part of an aerosol outlet path sealably passing through the liquid reservoir between the atomizer outlet and the aerosol outlet, wherein liquid reservoir is also partially defined between the interior of the cartridge housing and the chimney;*

*a resilient seal disposed between an exterior of the chimney and the interior of the cartridge housing, the resilient seal sealing an upper end of the liquid reservoir and locating the chimney within the cartridge housing;*

*an atomizer disposed within the atomizing chamber, the atomizer comprising a resistive heating element;*

*a wick in contact with the atomization liquid in the liquid reservoir through the first wick aperture and the second wick aperture, the wick passing through the open central passage between the wick apertures at opposite sides of the atomizing chamber, the wick comprising a first wick end passing through the first wick aperture and a second wick end passing through the second wick aperture; and*

*an atomizing assembly engaged with the atomizing chamber, the atomizing assembly having a pair of semicircular recesses formed therein, the pair of semicircular recesses aligning cooperatively with the first wick aperture and the second wick aperture of the atomizing chamber to result in a pair of circular apertures through which the first wick end and the second wick end pass with a compressive fit, the atomizing assembly comprising the atomizer.*

*53. An electronic cigarette comprising:*

*a power supply portion comprising a rechargeable battery; and*

*a cartridge configured for separable attachment to the power supply portion; the cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture at opposite sides of the atomizing chamber, the atomizing chamber defining an open central passage;*

*a non-porous liquid reservoir at least partially defined by an interior of the cartridge housing and an exterior of the atomizing chamber, the liquid reservoir configured to contain an atomization liquid, the liquid reservoir comprising a clear or translucent window to an exterior of the cartridge housing, the clear or translucent window allowing visual determination of a liquid level within the liquid reservoir;*

*a chimney formed as a single unit with the atomizing chamber, the chimney forming at least part of an aerosol outlet path sealably passing through the liquid reservoir between the atomizer outlet and the aerosol outlet, wherein liquid reservoir is also partially defined between the interior of the cartridge housing and the chimney;*

*a resilient seal disposed between an exterior of the chimney and the interior of the cartridge housing, the resilient seal sealing an upper end of the liquid reservoir and locating the chimney within the cartridge housing;*

*an atomizer disposed within the atomizing chamber, the atomizer comprising a resistive heating element;*

*a wick in contact with the atomization liquid in the liquid reservoir through the first wick aperture and the second wick aperture, the wick passing through the open central passage between the wick apertures at opposite sides of the atomizing chamber, the wick comprising a first wick end passing through the first*

*wick aperture and a second wick end passing through the second wick aperture; and*

*an atomizing assembly engaged with the atomizing chamber, the atomizing assembly having a pair of semicircular recesses formed therein, the pair of semicircular recesses aligning cooperatively with the first wick aperture and the second wick aperture of the atomizing chamber to result in a pair of circular apertures through which the first wick end and the second wick end pass with a compressive fit, the atomizing assembly comprising the atomizer.*

*54. A cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture at opposite sides of the atomizing chamber;*

*a liquid reservoir at least partially defined by an interior of the cartridge housing and an exterior of the atomizing chamber, the liquid reservoir configured to contain an atomization liquid;*

*a chimney formed as a single unit with the atomizing chamber, the chimney forming at least part of an aerosol outlet path sealably passing through the reservoir between the atomizer outlet and the aerosol outlet;*

*an atomizer disposed within the atomizing chamber, the atomizer comprising a resistive heating element; and*

*a wick in contact with the atomization liquid in the liquid reservoir through the first wick aperture and the second wick aperture, the wick disposed between the liquid reservoir and the atomizer.*

*55. An electronic cigarette comprising:*

*a power supply portion comprising a rechargeable battery; and*

*a cartridge configured for separable attachment to the power supply portion; the cartridge comprising:*

*a cartridge housing;*

*a mouthpiece end comprising an aerosol outlet;*

*an atomizing chamber disposed within the cartridge housing proximate a lower end of the cartridge housing opposite the mouthpiece end, the atomizing chamber comprising an atomizer outlet and an atomizing chamber air inlet; the atomizing chamber further comprising a first wick aperture and a second wick aperture at opposite sides of the atomizing chamber;*

*a liquid reservoir at least partially defined by an interior of the cartridge housing and an exterior of the atomizing chamber, the liquid reservoir configured to contain an atomization liquid;*

*a chimney formed as a single unit with the atomizing chamber, the chimney forming at least part of an aerosol outlet path sealably passing through the reservoir between the atomizer outlet and the aerosol outlet;*

*an atomizer disposed within the atomizing chamber, the atomizer comprising a resistive heating element; and*

*a wick in contact with the atomization liquid in the liquid reservoir through the first wick aperture and the second wick aperture, the wick disposed between the liquid reservoir and the atomizer.*

*56. The cartridge of claim 41, wherein the liquid reservoir is sealably separated from the atomizing chamber.*

*57. The cartridge of claim 41, wherein the liquid reservoir is partially defined between the interior of the cartridge housing and the chimney.*

*58. The cartridge of claim 41, wherein the chimney is formed as a single unit with the atomizing chamber.*

*59. The cartridge of claim 41, further comprising a resilient seal disposed between an exterior of the chimney and the interior of the cartridge housing, the resilient seal sealing an upper end of the liquid reservoir and locating the chimney within the cartridge housing.*

*60. The cartridge of claim 41, wherein the liquid reservoir is not a porous reservoir.*

*61. The cartridge of claim 41, further comprising an atomizer assembly comprising the atomizer, the atomizer assembly closing the lower end of the cartridge housing.*

*62. The cartridge of claim 41, wherein the wick comprises a bundle of heat resistant fibers.*

*63. The cartridge of claim 41, wherein the wick comprises a first wick end passing through the first wick aperture and a second wick end passing through the second wick aperture.*

*64. The cartridge of claim 63, wherein a middle part of the wick is positioned to be heated by the resistive heating element when current passes through the resistive heating element, and wherein the first wick end and the second wick end are outside the atomizing chamber and in contact with the atomization liquid in the liquid reservoir.*

*65. The cartridge of claim 63, further comprising an atomizing assembly engaged with the atomizing chamber, the atomizing assembly having a pair of semicircular recesses formed therein, the pair of semicircular recesses aligning cooperatively with the first wick aperture and the second wick aperture of the atomizing chamber to result in opposed circular apertures through which the first wick end and the second wick end pass with a compressive fit.*

*66. The cartridge of claim 65, wherein the atomizing assembly comprises the atomizer.*

*67. The cartridge of claim 41, wherein the wick is configured to transfer the atomization liquid by capillarity from the liquid reservoir to the atomizer.*

*68. The cartridge of claim 41, wherein the resistive heating element comprises a coiled nickel-chromium heater through which the wick passes.*

*69. The cartridge of claim 41, wherein the atomizing chamber defines an open central passage, and wherein the wick passes through the open central passage between the wick apertures at opposite sides of the atomizing chamber.*

*70. The cartridge of claim 41, wherein the atomizing chamber comprises an open atomization chamber, and wherein the wick causes capillarity-driven transfer of the atomization liquid from the liquid reservoir to the open atomization chamber in a controlled manner without flooding the open atomization chamber.*

*71. The cartridge of claim 41, further comprising:*

*an inlet vent formed on the exterior of the housing and coupled to deliver air to the atomizing chamber air inlet.*

*72. The cartridge of claim 71, wherein the inlet vent is coupled to the atomizing chamber air inlet by a conduit.*

*73. The cartridge of claim 72, wherein the conduit sealably passes through the liquid reservoir.*

*74. The cartridge of claim 41, further comprising the atomization liquid.*

*75. The cartridge of claim 43, wherein the chimney is formed as a single unit with the atomizing chamber.*

*76. The cartridge of claim 43, wherein the liquid reservoir is sealably separated from the atomizing chamber.*

*77. The cartridge of claim 43, wherein the liquid reservoir is partially defined between the interior of the cartridge housing and the chimney.*

*78. The cartridge of claim 43, further comprising a resilient seal disposed between an exterior of the chimney and the interior of the cartridge housing, the resilient seal sealing an upper end of the liquid reservoir and locating the chimney within the cartridge housing.*

*79. The cartridge of claim 43, wherein the liquid reservoir is not a porous reservoir.*

*80. The cartridge of claim 43, wherein the liquid reservoir comprises a clear or translucent window to an exterior of the cartridge housing, the clear or translucent window allowing visual determination of a liquid level within the liquid reservoir.*

*81. The cartridge of claim 43, further comprising an atomizer assembly comprising the atomizer, the atomizer assembly closing the lower end of the cartridge housing.*

*82. The cartridge of claim 43, wherein the wick comprises a bundle of heat resistant fibers.*

*83. The cartridge of claim 43, wherein the first wick aperture and the second wick aperture are at opposite sides of the atomizing chamber.*

*84. The cartridge of claim 43, wherein the wick comprises a first wick end passing through the first wick aperture and a second wick end passing through the second wick aperture.*

*85. The cartridge of claim 84, wherein a middle part of the wick is positioned to be heated by the resistive heating element when current passes through the resistive heating element, and wherein the first wick end and the second wick end are outside the atomizing chamber and in contact with the atomization liquid in the liquid reservoir.*

*86. The cartridge of claim 43, wherein the wick is configured to transfer the atomization liquid by capillarity from the liquid reservoir to the atomizer.*

*87. The cartridge of claim 43, wherein the resistive heating element comprises a coiled nickel-chromium heater through which the wick passes.*

*88. The cartridge of claim 43, wherein the atomizing chamber defines an open central passage, and wherein the wick passes through the open central passage between the wick apertures at opposite sides of the atomizing chamber.*

*89. The cartridge of claim 43, wherein the atomizing chamber comprises an open atomization chamber, and wherein the wick causes capillarity-driven transfer of the atomization liquid from the liquid reservoir to the open atomization chamber in a controlled manner without flooding the open atomization chamber.*

*90. The cartridge of claim 43, further comprising:*

*an inlet vent formed on the exterior of the housing and coupled to deliver air to the atomizing chamber air inlet.*

*91. The cartridge of claim 90, wherein the inlet vent is coupled to the atomizing chamber air inlet by a conduit.*

*92. The cartridge of claim 91, wherein the conduit sealably passes through the liquid reservoir.*

*93. The cartridge of claim 43, further comprising the atomization liquid.*

*94. The cartridge of claim 45, further comprising:*

*a cartridge housing having a lower end and the mouthpiece end, the mouthpiece end being opposite the lower end;*

*wherein the atomizing chamber is disposed within the cartridge housing proximate the lower end of the cartridge housing.*

*95. The cartridge of claim 94, wherein the liquid reservoir is within the cartridge housing.*

*96. The cartridge of claim 95, wherein the liquid reservoir is sealably separated from the atomizing chamber.*

*97. The cartridge of claim 94, wherein the atomizing chamber further comprises an atomizing chamber air inlet, and wherein the atomizing chamber air inlet is closer to the lower end of the cartridge housing and the atomizer outlet is closer to the mouthpiece end.*

*98. The cartridge of claim 97, further comprising:*

*an inlet vent formed on the exterior of the cartridge housing and coupled to deliver air to the atomizing chamber air inlet.*

*99. The cartridge of claim 94, further comprising a resilient seal disposed between an exterior of the chimney and an interior of the cartridge housing, the resilient seal sealing an upper end of the liquid reservoir and locating the chimney within the cartridge housing.*

*100. The cartridge of claim 45, wherein the chimney passes through the liquid reservoir between the atomizer outlet and the aerosol outlet.*

*101. The cartridge of claim 45, wherein the chimney is formed as a single unit with the atomizing chamber.*

*102. The cartridge of claim 45, wherein the atomizing chamber defines an open central passage, and wherein the wick passes through the open central passage between the first wick aperture and the second wick aperture.*

*103. The cartridge of claim 102, wherein the first wick aperture and the second wick aperture are disposed on opposite sides of the atomizing chamber.*

*104. The cartridge of claim 103, further comprising an atomizing assembly engaged with the atomizing chamber, the atomizing assembly having a pair of semicircular recesses formed therein, the pair of semicircular recesses aligning cooperatively with the first wick aperture and the second wick aperture of the atomizing chamber to result in opposed circular apertures through which the first wick end and the second wick end pass with a compressive fit.*

*105. The cartridge of claim 104, wherein the atomizing assembly comprises the atomizer.*

*106. The cartridge of claim 104, wherein the atomizing assembly comprises an electrical coupler via which the electric current passes from the battery to the atomizer.*

*107. The cartridge of claim 45, wherein the atomizer comprises a resistive heating element.*

*108. The cartridge of claim 107, wherein the resistive heating element comprises a coiled heater through which the wick passes.*

*109. The cartridge of claim 107, wherein the resistive heating element comprises nickel-chromium.*

*110. The cartridge of claim 46, wherein the chimney is formed as a single unit with the atomizing chamber.*

*111. The cartridge of claim 46, wherein the liquid reservoir is sealably separated from the atomizing chamber.*

*112. The cartridge of claim 46, wherein the liquid reservoir is partially defined between the interior of the cartridge housing and the chimney.*

*113. The cartridge of claim 46, further comprising a resilient seal disposed between an exterior of the chimney and the interior of the cartridge housing, the resilient seal sealing an upper end of the liquid reservoir and locating the chimney within the cartridge housing.*

*114. The cartridge of claim 46, wherein the liquid reservoir is not a porous reservoir.*

*115. The cartridge of claim 46, wherein the liquid reservoir comprises a clear or translucent window to an exterior of the cartridge housing, the clear or translucent window allowing visual determination of a liquid level within the liquid reservoir.*

*116. The cartridge of claim 46, further comprising an atomizer assembly comprising the atomizer, the atomizer assembly closing the lower end of the cartridge housing.*

*117. The cartridge of claim 46, wherein the wick comprises a bundle of heat resistant fibers.*

*118. The cartridge of claim 46, wherein the wick comprises a first wick end passing through the first wick aperture and a second wick end passing through the second wick aperture.*

*119. The cartridge of claim 118, wherein a middle part of the wick is positioned to be heated by the resistive heating element when current passes through the resistive heating element, and wherein the first wick end and the second wick end are outside the atomizing chamber and in contact with the atomization liquid in the liquid reservoir.*

*120. The cartridge of claim 118, further comprising an atomizing assembly engaged with the atomizing chamber, the atomizing assembly having a pair of semicircular recesses formed therein, the pair of semicircular recesses aligning cooperatively with the first wick aperture and the second wick aperture of the atomizing chamber to result in opposed circular apertures through which the first wick end and the second wick end pass with a compressive fit.*

*121. The cartridge of claim 120, wherein the atomizing assembly comprises the atomizer.*

*122. The cartridge of claim 46, wherein the wick is configured to transfer the atomization liquid by capillarity from the liquid reservoir to the atomizer.*

*123. The cartridge of claim 46, wherein the resistive heating element comprises a coiled nickel-chromium heater through which the wick passes.*

*124. The cartridge of claim 46, wherein the atomizing chamber defines an open central passage, and wherein the wick passes through the open central passage between the wick apertures at opposite sides of the atomizing chamber.*

*125. The cartridge of claim 46, wherein the atomizing chamber comprises an open atomization chamber, and wherein the wick causes capillarity-driven transfer of the atomization liquid from the liquid reservoir to the open atomization chamber in a controlled manner without flooding the open atomization chamber.*

*126. The cartridge of claim 46, further comprising:*

*an inlet vent formed on the exterior of the cartridge housing and coupled to deliver air to the atomizing chamber air inlet.*

*127. The cartridge of claim 126, wherein the inlet vent is coupled to the atomizing chamber air inlet by a conduit.*

*128. The cartridge of claim 127, wherein the conduit sealably passes through the liquid reservoir.*

*129. The cartridge of claim 46, further comprising the atomization liquid.*

*130. The cartridge of claim 48, wherein the liquid reservoir is sealably separated from the atomizing chamber.*

*131. The cartridge of claim 48, wherein the liquid reservoir is partially defined between the interior of the cartridge housing and the chimney.*

*132. The cartridge of claim 48, wherein the chimney is formed as a single unit with the atomizing chamber.*

*133. The cartridge of claim 48, wherein the liquid reservoir is not a porous reservoir.*

*134. The cartridge of claim 48, wherein the liquid reservoir comprises a clear or translucent window to an exterior of the cartridge housing, the clear or translucent window allowing visual determination of a liquid level within the liquid reservoir.*

*135. The cartridge of claim 48, further comprising an atomizer assembly comprising the atomizer, the atomizer assembly closing the lower end of the cartridge housing.*

*136. The cartridge of claim 48, wherein the wick comprises a bundle of heat resistant fibers.*

*137. The cartridge of claim 48, wherein the wick comprises a first wick end passing through the first wick aperture and a second wick end passing through the second wick aperture.*

*138. The cartridge of claim 137, wherein a middle part of the wick is positioned to be heated by the resistive heating element when current passes through the resistive heating element, and wherein the first wick end and the second wick end are outside the atomizing chamber and in contact with the atomization liquid in the liquid reservoir.*

*139. The cartridge of claim 137, further comprising an atomizing assembly engaged with the atomizing chamber, the atomizing assembly having a pair of semicircular recesses formed therein, the pair of semicircular recesses aligning cooperatively with the first wick aperture and the second wick aperture of the atomizing chamber to result in opposed circular apertures through which the first wick end and the second wick end pass with a compressive fit.*

*140. The cartridge of claim 139, wherein the atomizing assembly comprises the atomizer.*

*141. The cartridge of claim 48, wherein the wick is configured to transfer the atomization liquid by capillarity from the liquid reservoir to the atomizer.*

*142. The cartridge of claim 48, wherein the resistive heating element comprises a coiled nickel-chromium heater through which the wick passes.*

*143. The cartridge of claim 48, wherein the atomizing chamber defines an open central passage, and wherein the wick passes through the open central passage between the wick apertures at opposite sides of the atomizing chamber.*

*144. The cartridge of claim 48, wherein the atomizing chamber comprises an open atomization chamber, and wherein the wick causes capillarity-driven transfer of the atomization liquid from the liquid reservoir to the open atomization chamber in a controlled manner without flooding the open atomization chamber.*

*145. The cartridge of claim 48, further comprising:*

*an inlet vent formed on the exterior of the cartridge housing and coupled to deliver air to the atomizing chamber air inlet.*

*146. The cartridge of claim 145, wherein the inlet vent is coupled to the atomizing chamber air inlet by a conduit.*

*147. The cartridge of claim 146, wherein the conduit sealably passes through the liquid reservoir.*

*148. The cartridge of claim 48, further comprising the atomization liquid.*

*149. The cartridge of claim 50, wherein the liquid reservoir is sealably separated from the atomizing chamber.*

*150. The cartridge of claim 50, wherein the liquid reservoir is partially defined between the interior of the cartridge housing and the chimney.*

*151. The cartridge of claim 50, wherein the liquid reservoir is not a porous reservoir.*

*152. The cartridge of claim 50, wherein the atomizer assembly closes the lower end of the cartridge housing.*

*153. The cartridge of claim 50, wherein the wick comprises a bundle of heat resistant fibers.*

*154. The cartridge of claim 50, wherein a middle part of the wick is positioned to be heated by the resistive heating element when current passes through the resistive heating element.*

*155. The cartridge of claim 50, wherein the first wick end and the second wick end are outside the atomizing chamber and in contact with the atomization liquid in the liquid reservoir.*

*156. The cartridge of claim 50, wherein the wick is configured to transfer the atomization liquid by capillarity from the liquid reservoir to the atomizer.*

*157. The cartridge of claim 50, wherein the resistive heating element comprises a coiled nickel-chromium heater through which the wick passes.*

*158. The cartridge of claim 50, wherein the atomizing chamber defines an open central passage, and wherein the wick passes through the open central passage between the wick apertures at opposite sides of the atomizing chamber.*

*159. The cartridge of claim 50, wherein the atomizing chamber comprises an open atomization chamber, and wherein the wick causes capillarity-driven transfer of the atomization liquid from the liquid reservoir to the open atomization chamber in a controlled manner without flooding the open atomization chamber.*

*160. The cartridge of claim 50, further comprising:*

*an inlet vent formed on the exterior of the cartridge housing and coupled to deliver air to the atomizing chamber air inlet.*

*161. The cartridge of claim 160, wherein the inlet vent is coupled to the atomizing chamber air inlet by a conduit.*

*162. The cartridge of claim 161, wherein the conduit sealably passes through the liquid reservoir.*

*163. The cartridge of claim 50, wherein the atomizing assembly comprises the atomizer.*

*164. The cartridge of claim 50, further comprising the atomization liquid.*

*165. The cartridge of claim 52, wherein the liquid reservoir is sealably separated from the atomizing chamber.*

*166. The cartridge of claim 52, wherein the atomizer assembly closes the lower end of the cartridge housing.*

*167. The cartridge of claim 52, wherein the wick comprises a bundle of heat resistant fibers.*

*168. The cartridge of claim 52, wherein a middle part of the wick is positioned to be heated by the resistive heating element when current passes through the resistive heating element.*

*169. The cartridge of claim 52, wherein the first wick end and the second wick end are outside the atomizing chamber and in contact with the atomization liquid in the liquid reservoir.*

*170. The cartridge of claim 52, wherein the wick is configured to transfer the atomization liquid by capillarity from the liquid reservoir to the atomizer.*

*171. The cartridge of claim 52, wherein the resistive heating element comprises a coiled nickel-chromium heater through which the wick passes.*

*172. The cartridge of claim 52, wherein the atomizing chamber comprises an open atomization chamber, and wherein the wick causes capillarity-driven transfer of the atomization liquid from the liquid reservoir to the open atomization chamber in a controlled manner without flooding the open atomization chamber.*

*173. The cartridge of claim 52, further comprising:*

*an inlet vent formed on the exterior of the cartridge housing and coupled to deliver air to the atomizing chamber air inlet.*

*174. The cartridge of claim 173, wherein the inlet vent is coupled to the atomizing chamber air inlet by a conduit.*

*175. The cartridge of claim 174, wherein the conduit sealably passes through the liquid reservoir.*

*176. The cartridge of claim 52, further comprising the atomization liquid.*

*177. The cartridge of claim 54, wherein the liquid reservoir is sealably separated from the atomizing chamber.*

*178. The cartridge of claim 54, wherein the liquid reservoir is partially defined between the interior of the cartridge housing and the chimney.*

*179. The cartridge of claim 54, further comprising a resilient seal disposed between an exterior of the chimney and the interior of the housing, the resilient seal sealing an upper end of the liquid reservoir and locating the chimney within the cartridge housing.*

*180. The cartridge of claim 54, wherein the liquid reservoir is not a porous reservoir.*

*181. The cartridge of claim 54, wherein the liquid reservoir comprises a clear or translucent window to an exterior of the cartridge housing, the clear or translucent window allowing visual determination of a liquid level within the liquid reservoir.*

*182. The cartridge of claim 54, further comprising an atomizer assembly comprising the atomizer, the atomizer assembly closing the lower end of the cartridge housing.*

*183. The cartridge of claim 54, wherein the wick comprises a bundle of heat resistant fibers.*

*184. The cartridge of claim 54, wherein the wick comprises a first wick end passing through the first wick aperture and a second wick end passing through the second wick aperture.*

*185. The cartridge of claim 184, wherein a middle part of the wick is positioned to be heated by the resistive heating element when current passes through the resistive heating element, and wherein the first wick end and the second wick end are outside the atomizing chamber and in contact with the atomization liquid in the liquid reservoir.*

*186. The cartridge of claim 184, further comprising an atomizing assembly engaged with the atomizing chamber, the atomizing assembly having a pair of semicircular recesses formed therein, the pair of semicircular recesses aligning cooperatively with the first wick aperture and the second wick aperture of the atomizing chamber to result in opposed circular apertures through which the first wick end and the second wick end pass with a compressive fit.*

*187. The cartridge of claim 186, wherein the atomizing assembly comprises the atomizer.*

*188. The cartridge of claim 54, wherein the wick is configured to transfer the atomization liquid by capillarity from the liquid reservoir to the atomizer.*

*189. The cartridge of claim 54, wherein the resistive heating element comprises a coiled nickel-chromium heater through which the wick passes.*

*190. The cartridge of claim 54, wherein the atomizing chamber defines an open central passage, and wherein the wick passes through the open central passage between the wick apertures at opposite sides of the atomizing chamber.*

*191. The cartridge of claim 54, wherein the atomizing chamber comprises an open atomization chamber, and wherein the wick causes capillarity-driven transfer of the atomization liquid from the liquid reservoir to the open atomization chamber in a controlled manner without flooding the open atomization chamber.*

*192. The cartridge of claim 54, further comprising:*

*an inlet vent formed on the exterior of the cartridge housing and coupled to deliver air to the atomizing chamber air inlet.*

*193. The cartridge of claim 192, wherein the inlet vent is coupled to the atomizing chamber air inlet by a conduit.*

*194. The cartridge of claim 193, wherein the conduit sealably passes through the liquid reservoir.*

*195. The cartridge of claim 54, further comprising the atomization liquid.*

*196. An electronic cigarette comprising:*

*a power supply portion comprising the battery; and*

*the cartridge of claim 45, the cartridge configured for separable attachment to the power supply portion.*

* * * * *